United States Patent [19]
Förster

[11] Patent Number: 4,545,760
[45] Date of Patent: Oct. 8, 1985

[54] ORTHODONTIC DEVICE

[75] Inventor: Rolf Förster, Pforzheim, Fed. Rep. of Germany

[73] Assignee: Bernhard Forster GmbH, Pforzheim, Fed. Rep. of Germany

[21] Appl. No.: 580,819

[22] Filed: Feb. 16, 1984

[30] Foreign Application Priority Data

Mar. 8, 1983 [DE] Fed. Rep. of Germany ....... 3308104

[51] Int. Cl.⁴ .............................................. A61C 3/00
[52] U.S. Cl. ......................................... 433/18; 433/9
[58] Field of Search ..................... 433/9, 8, 10, 11, 13, 433/15, 16, 18

[56] References Cited

U.S. PATENT DOCUMENTS

| | | | |
|---|---|---|---|
| 2,701,913 | 2/1955 | Lane | 433/16 |
| 3,218,715 | 11/1965 | Wallshein | 433/16 |
| 4,068,379 | 1/1978 | Miller et al. | 433/9 |
| 4,243,386 | 1/1981 | Kawaguchi | 433/9 |
| 4,268,249 | 5/1981 | Forster | 433/10 |
| 4,386,908 | 6/1983 | Kurz | 433/9 |

Primary Examiner—John J. Wilson
Attorney, Agent, or Firm—Balogh, Osann, Kramer, Dvorak, Genova & Traub

[57] ABSTRACT

This invention relates to a wire-tensioning and/or -fixing orthodontic device comprising a bracket having preferably a bearing eye, a wire-engaging shoulder, and a retaining member which is rotatably mounted in the bearing eye and adapted to retain a correcting wire in engagement with said wire-engaging shoulder. For use in the lingual technique, the orthodontic device can be further miniaturized in that the base portion of the bracket has no flange arms and is secured to a backing pad and the latter is provided on the side opposite to the bracket with a metal fabric adapted to be adhesively fixed to a tooth. The backing pad comprises outwardly extending side arms (rotation-inducing arms, adaptation-inducing arms and activating arms), which are adapted to be activated by being bent.

9 Claims, 10 Drawing Figures

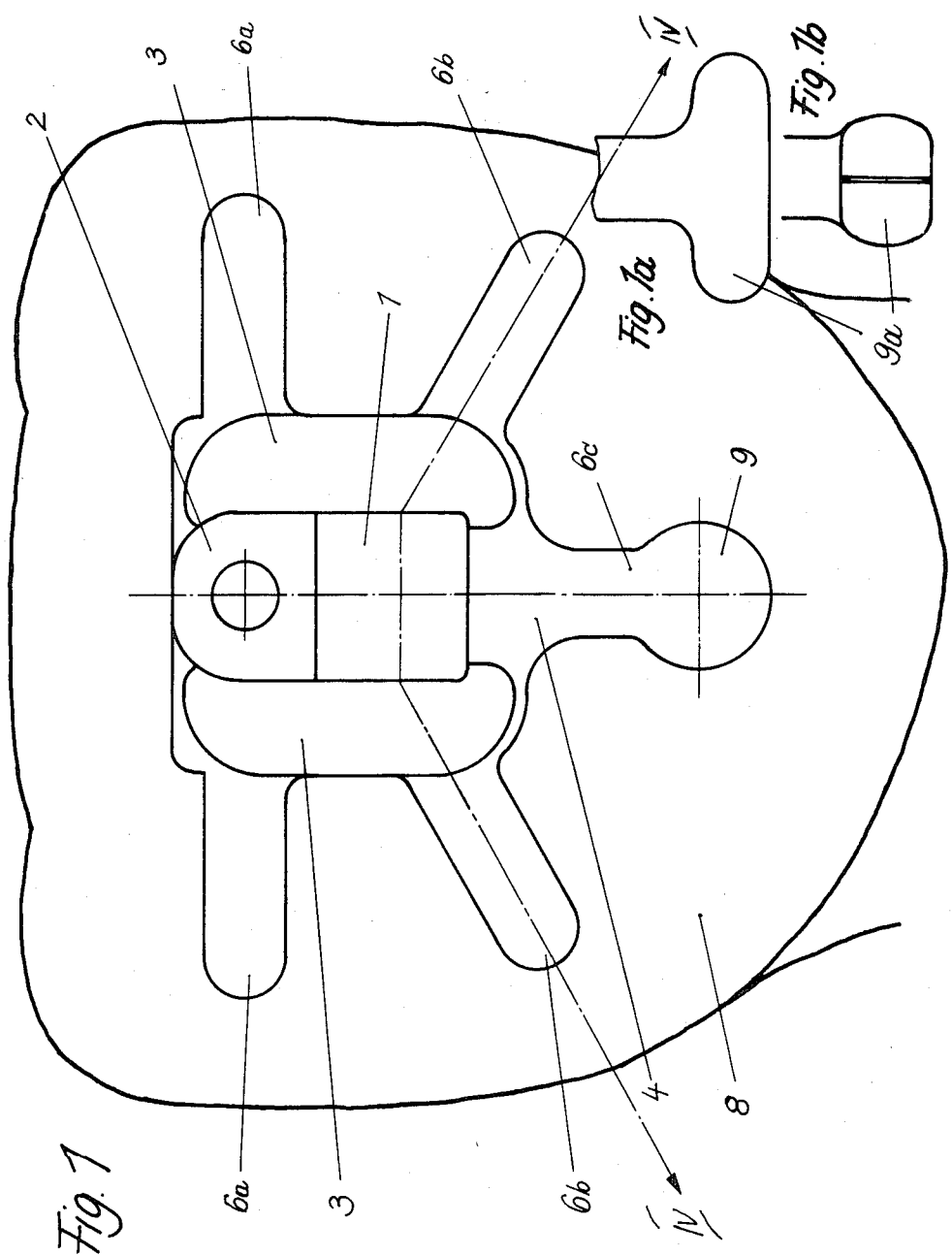

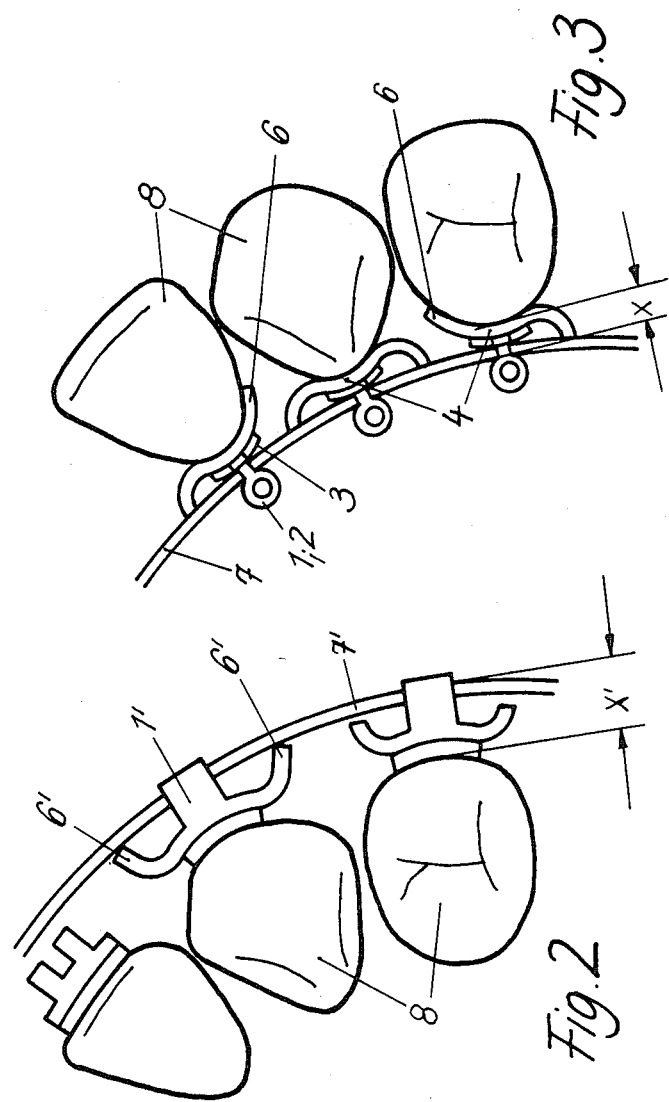

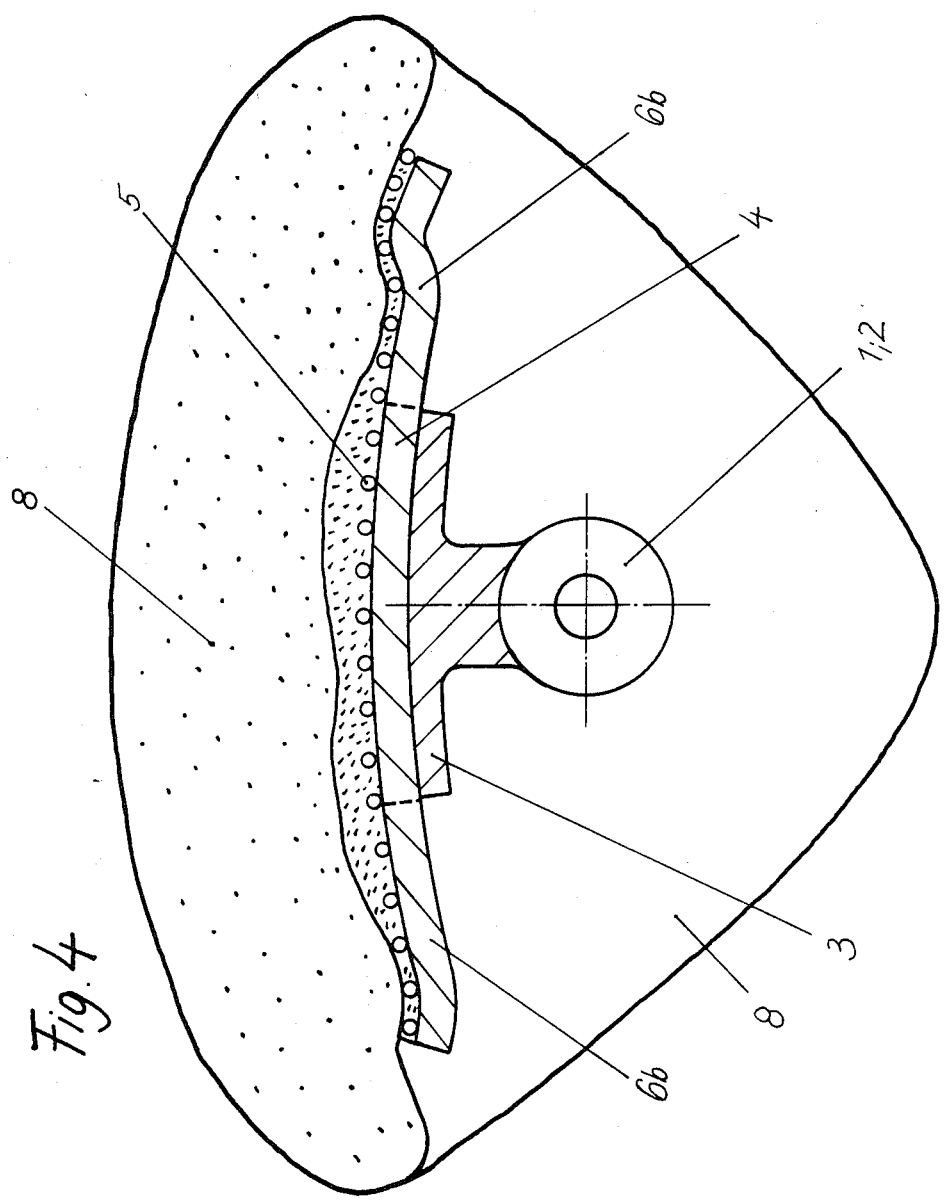

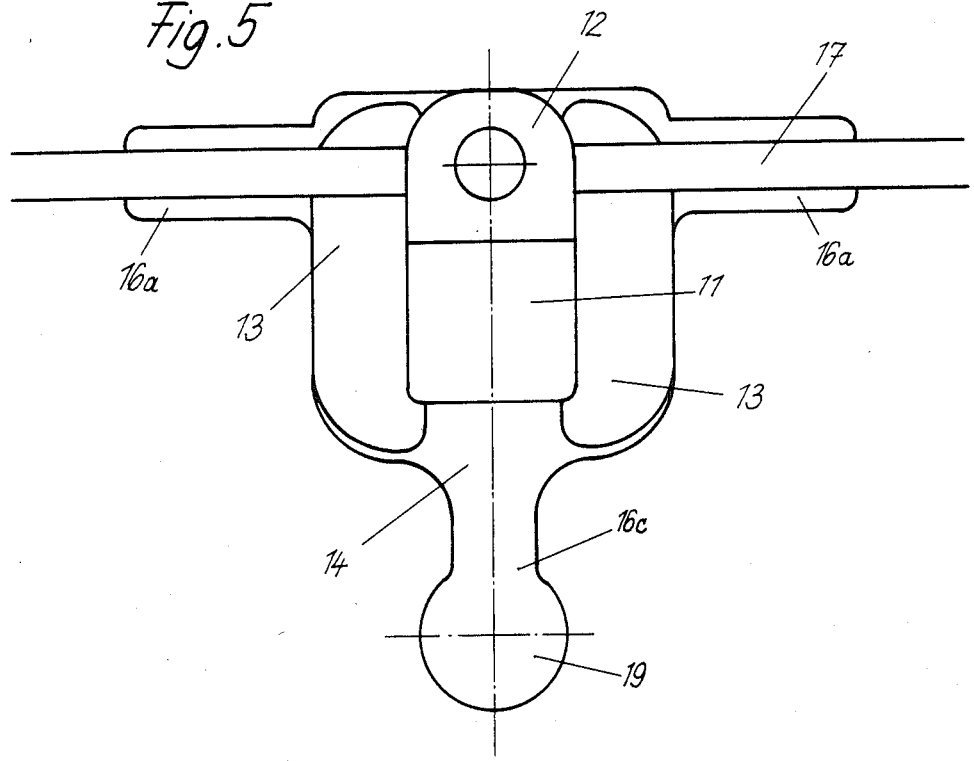
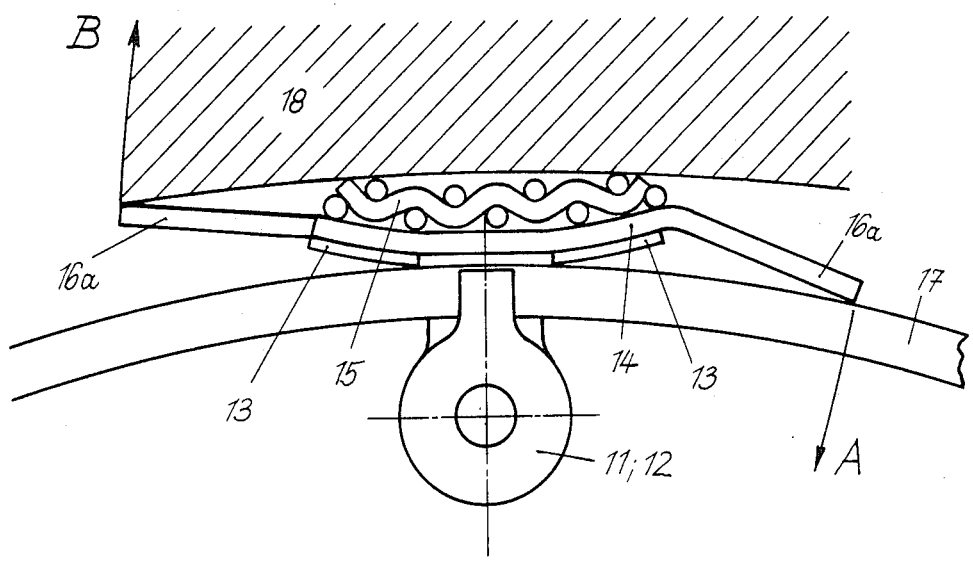

4,14    5,15

4',14'    5',15'

ORTHODONTIC DEVICE

This invention relates to a wire-tensioning and/or wire-fixing orthodontic device, which comprises a bracket preferably provided with a bearing eye, a wire-engaging shoulder, and a retaining member which is rotatably mounted in the bearing eye and adapted to retain a correcting wire in engagement with said wire-engaging shoulder.

The provision of such bracket having a bearing eye and a wire-engaging shoulder is known from German Patent Specification Nos. 28 21 127 and 29 19 640 and the corresponding U.S. Pat. Nos. 4,196,517 and 4,268,249.

It is an object of the invention so to improve such orthodontic devices, particularly those having brackets of the type disclosed in German Patent Specification Nos. 28 21 127 and 29 19 640, that they are further miniaturized and can have a greater utility for the so-called lingual technique. That term describes an orthodontic technique in which the brackets for tensioning and fixing the correcting wire are not adhesively joined to the teeth on the outside thereof but on the inside so that the brackets are invisible and the teeth to be corrected are acted upon on their inside surfaces. To be suitable for that purpose, the brackets must be as small and as low as possible and rounded on all sides because the high sensitivity of the patient's tongue requires the brackets to be attached to the inside surface of the teeth in such a manner that they will not be disturbing to the tongue contacting the inner dental arch.

SUMMARY OF INVENTION

In a wire-tensioning and/or -fixing orthodontic device, which preferably has a mounting bearing eye, a wire-engaging shoulder, and a retaining member which is rotatably mounted in the bearing eye and adapted to retain a correcting wire in engagement with the wire-engaging shoulder, that object is accomplished in that a bracket of the device comprises a base portion having no flange arms and the device also comprises a backing pad provided with a metal fabric, which is adapted to be adhesively fixed to a tooth, and the backing pad is also provided with outwardly extending side arms, which are adapted to be bent to an operative position. In that device the bracket having no flange arms has a smaller height and the functions previously performed by the flange arms of the bracket are now performed by the side arms of the backing pad. Further details are apparent from the following description and the accompanying drawings.

The metal fabric provided on the backing pad may be roughened by sandblasting in order to improve its adhesion. As a result, a device which is required to have a given resistance to shearing forces when it has been adhesively fixed can be further miniaturized.

BRIEF DESCRIPTION OF THE DRAWINGS

Preferred embodiments of the adhesively fixable orthodontic devices according to the invention are shown on the drawings, in which:

FIG. 1 is an elevation showing an orthodontic device according to a first embodiment and FIGS. 1a and 1b are fragmentary elevations showing portions of the orthodontic device of FIG. 1 after the lugs 9a have been stamped and bent, respectively, FIGS. 2 and 3 are two top plan views illustrating the use of the orthodontic device for the facial technique and of the miniaturized orthodontic device for the lingual technique, FIG. 4 is a vertical sectional view taken on line IV—IV in FIG. 1, FIGS. 5 and 6 are, respectively, an elevation and top plan view showing a second embodiment of the orthodontic device

DESCRIPTION OF THE PREFERRED EMBODIMENT OF THE INVENTION

Figure 7:
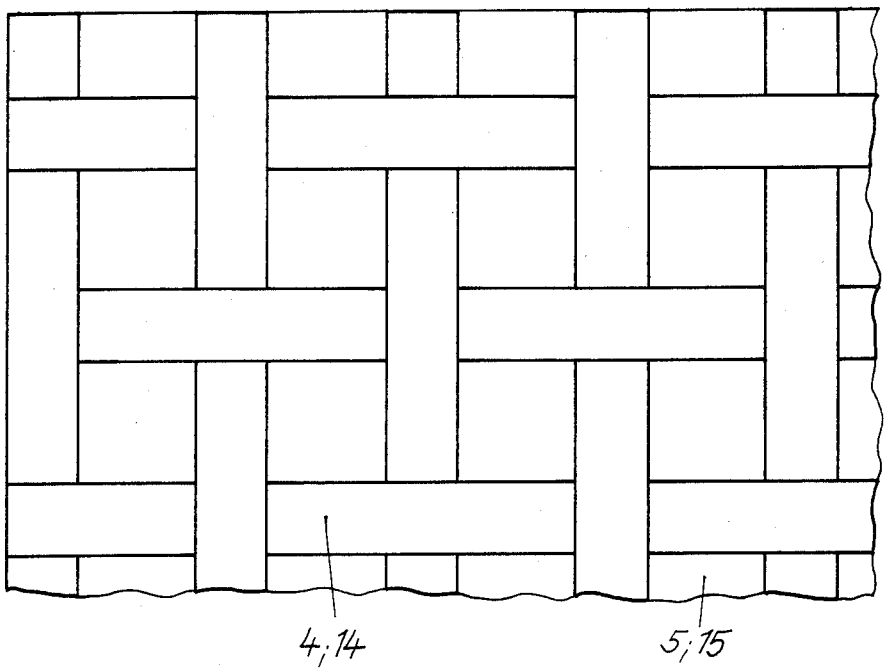
FIGS. 7 and 8 are respective top plan views showing the metal fabric before and after the sandblasting.

The bracket 1 shown in FIGS. 1 to 4 is provided with a retaining member 2 as disclosed in German Patent Specification No. 28 21 127 and comprises a base portion 3 that is directly secured to a backing pad 4, which is provided with a metal fabric 5. In the present embodiment the backing pad 4 is provided with outwardly protruding side arms 6, which when the orthodontic device has been installed serve as rotation-inducing arms 6a disposed on both sides, downwardly inclined adaptation-inducing arms 6b on both sides, and a depending activating arm 6c. When the side arms have been activated in that they have been bent in accordance with FIGS. 3 and 4 relative to the inner arch wire 7 and the tooth 8, the rotation-inducing arms 6a serve to impart a torque in the distal or mesial direction, depending on the side of engagement, or to induce a buccal or labial movement when both arms have been activated. It is apparent from FIG. 1 that the side arms 6 protrude like feet of a sea urchin.

The depending side arm 6c is arched and extends toward the gums to serve as an activating arm and has an enlarged end portion 9 for an activating connection, e.g., by means of a rubber band, to the adjacent teeth in order to improve the occlusion of the teeth. In accordance with FIGS. 1a and 1b the enlarged end portion 9 may have a spherical shape owing to the provision of inturned lugs 9a.

As is apparent upon a comparison of FIGS. 2 and 3 the distance x in the orthodontic devices 1 to 6 used for the labial technique (inner arch technique) is smaller than the corresponding distance x' in the orthodontic devices 1', 6', 7' used for the facial technique (outer arch technique) because the flange arms 6' of the bracket 1' provided with outer arch wire 7' have been replaced by side arms 6, which are directly provided on the backing pad 4, which is provided with a metal fabric 5 for adhesively fixing the orthodontic device. The side arms 6 cooperate with the inner arch wire 7.

In accordance with the sectional view of FIG. 4, the orthodontic device comprising the bracket 1, 2 provided with a base portion 3, the backing pad 4 and the metal fabric 5 has been adhesively secured to the tooth. The side arms 6b are used as adaptation-inducing arms and can be adjusted to the shapes of the teeth which vary greatly on the lingual side.

FIGS. 5 and 6 of the drawing show a bracket 11 provided with locking means 12 as disclosed in German Patent Specification 28 21 127 and a base portion 13. In addition to the bracket 11, the orthodontic device comprises a backing pad 14 and a metal fabric 15. In the present case the backing pad 14 is provided with only three side arms 16a, 16b and 16c in a cross-shaped arrangement. The inner arch wire 17 is activated in the direction indicated by the arrow A and serves to impart to the teeth 18 a rotation in the sense indicated by the arrow B. The side arm 16c extends toward the gums and has also an enlarged end portion 19.

Figure 8:
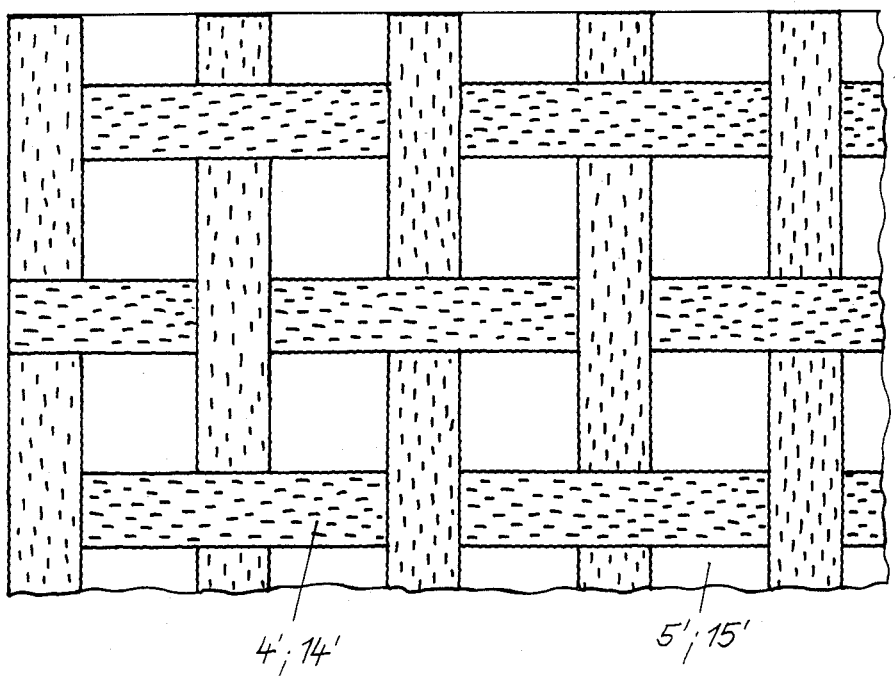

FIGS. 7 and 8 show a backing pad 4 or 14 provided with a metal fabric 5 or 15 before the roughening effected by sand blasting and the corresponding parts 4', 14' and 5', 15' after such roughening. The adhesion can be greatly increased by such roughening so that the brackets can be further miniaturized for a given retaining force.

What is claimed is:

1. In an orthodontic device comprising a backing pad and a bracket having a base portion secured to said backing pad on one side thereof, the improvement comprising said backing pad having laterally outwardly protruding, bendable side arms, said side arms comprising at least one activating arm having an enlarged end portion for an activating connection, and said backing pad being provided on the side thereof opposite to that secured to the base portion with a metal fabric adapted to be adhesively fixed to a tooth, said activating arm, when being installed in the mouth of a patient, being arched and extending downwardly towards the gum of said patient, and said enlarged end portion being engageable with an adjacent side arm of an adjacent similar orthodontic device when said orthodontic devices are used to improve the occlusion of adjacent teeth.

2. The improvement set forth in claim 1 as applied to an orthodontic device in which said bracket comprises a bearing eye, a wire-engaging shoulder, and a retaining member which is rotatably mounted in said bearing eye and adapted to retain a correcting wire in engagement with said wire-engaging shoulder.

3. The improvement set forth in claim 1 as applied to a wire-tensioning orthodontic device.

4. The improvement set forth in claim 1 as applied to a wire-fixing orthodontic device.

5. The improvement set forth in claim 1, wherein said enlarged end portion of said activating arm is spherical and provided with inturned lugs.

6. The improvement set forth in claim 1, wherein said backing pad is provided with three of said side arms in a cross-shaped pattern and said three side arms comprise two upper side arms which constitute rotation-inducing arms, and when said device has been secured to a tooth of a patient and installed in conjunction with a correcting wire extending on the inner dental arch of said patient said rotation-inducing arms are adapted to be bent into engagement with said correcting wire in order to impart by means of said correcting wire a torque to said tooth about its axis.

7. The improvement set forth in claim 1, wherein said backing pad is provided with five of said side arms including downwardly inclined adaptation-inducing arms and when said orthodontic device is secured to a tooth of a patient, and installed in conjunction with a correcting wire extending along the inner dental arch of said patient, said adaptation-inducing arms are bent into engagement with said correcting wire in order to effect an adaptation of said tooth.

8. The improvement set forth in claim 1, wherein said metal fabric has a rough surface facing away from said backing pad.

9. The improvement set forth in claim 8, wherein said rough surface has been roughened by sandblasting.

* * * * *